United States Patent
Miyazaki et al.

(10) Patent No.: US 7,635,671 B2
(45) Date of Patent: Dec. 22, 2009

(54) MICROBUBBLE WASHING COMPOSITION, MICROBUBBLE WASHING METHOD, AND MICROBUBBLE WASHING APPARATUS

(75) Inventors: Kazuo Miyazaki, Kanagawa (JP); Susumu Fujikawa, Tokyo (JP)

(73) Assignees: Towa Enzyme Co., Ltd, Kanagawa (JP); Thales Inc., Tokyo (JP)

(*) Notice: Subject to any disclaimer, the term of this patent is extended or adjusted under 35 U.S.C. 154(b) by 0 days.

(21) Appl. No.: 11/826,989

(22) Filed: Jul. 19, 2007

(65) Prior Publication Data

US 2008/0083440 A1    Apr. 10, 2008

(30) Foreign Application Priority Data

Oct. 6, 2006    (JP) .............................. 2006-274959

(51) Int. Cl.
  *C11D 4/72*    (2006.01)
  *B08B 3/04*    (2006.01)
(52) U.S. Cl. ..................... 510/320; 510/327; 510/341; 510/356; 510/361; 119/158; 119/159; 119/160; 119/606; 119/651
(58) Field of Classification Search ................. 510/320, 510/337, 341, 356, 361; 119/158, 159, 160, 119/606, 650, 651
See application file for complete search history.

(56) References Cited

U.S. PATENT DOCUMENTS

| | | | | |
|---|---|---|---|---|
| 2,691,636 A * | 10/1954 | Stayner | ...................... | 510/484 |
| 4,556,554 A | 12/1985 | Calvo | | |
| 5,078,898 A * | 1/1992 | Jars | .............................. | 510/392 |
| 5,160,655 A * | 11/1992 | Donker et al. | ................ | 510/303 |
| 5,347,665 A | 9/1994 | Kumon et al. | | |
| 5,448,966 A * | 9/1995 | McKinnon et al. | ........... | 119/676 |
| 5,454,982 A * | 10/1995 | Murch et al. | ................. | 510/350 |
| 5,657,719 A * | 8/1997 | Whan | .......................... | 119/263 |
| 5,769,029 A * | 6/1998 | Marshall | ...................... | 119/651 |
| 5,904,735 A * | 5/1999 | Gutierrez et al. | ................ | 8/137 |
| 6,106,828 A | 8/2000 | Bisgard-Frantzen et al. | | |
| 6,121,215 A | 9/2000 | Rau | | |
| 6,248,338 B1 * | 6/2001 | Muller et al. | ................ | 424/401 |
| 6,662,600 B1 * | 12/2003 | Field et al. | ................... | 68/17 R |
| 2002/0077265 A1 * | 6/2002 | Buzzacarini et al. | ......... | 510/296 |
| 2002/0128165 A1 * | 9/2002 | Baker et al. | .................. | 510/309 |
| 2002/0137654 A1 * | 9/2002 | Hage et al. | ................... | 510/392 |
| 2004/0151684 A1 | 8/2004 | Mori et al. | | |
| 2005/0026299 A1 | 2/2005 | Bhattacharjee et al. | | |

FOREIGN PATENT DOCUMENTS

| | | | |
|---|---|---|---|
| EP | 0 839 905 A1 | | 5/1998 |
| JP | 60-89413 A | | 5/1985 |
| JP | 62-238214 A | | 10/1987 |
| JP | 63-1-30514 A | | 6/1988 |
| JP | 2-69600 A | | 3/1990 |
| JP | 2-227500 A | | 9/1990 |
| JP | 2003126665 A | * | 5/2003 |
| JP | 2004-534528 A | | 11/2004 |
| JP | 2005-177119 A | | 7/2005 |
| JP | 2006-034473 | | 2/2006 |
| JP | 2006068631 A | * | 3/2006 |

OTHER PUBLICATIONS

Suvva Precision, "Micro Bubbles and its applications," Mar. 23, 2006, Retrieved from the Internet on Feb. 18, 2008, XP002469734.

* cited by examiner

*Primary Examiner*—Mark Eashoo
*Assistant Examiner*—M. Reza Asdjodi
(74) *Attorney, Agent, or Firm*—Birch, Stewart, Kolasch & Birch, LLP

(57) ABSTRACT

The present invention provides a microbubble washing composition for washing a human body or an animal, a microbubble washing method using the microbubble washing composition, and a microbubble washing apparatus suitable for carrying out the method are provided which are capable of safely removing sebum and old keratin adhering to the surfaces of the pores in a short period of time, keeping the skin clean for a long period of time, preventing an odor. Specifically, the present invention provides a microbubble washing composition for washing a human body or an animal including a protease and a lipase, a microbubble washing method for washing a human body or an animal including washing a human body or an animal using a washing liquid containing the washing composition and microbubbles, and a microbubble washing apparatus.

11 Claims, 1 Drawing Sheet

MICROBUBBLE WASHING COMPOSITION, MICROBUBBLE WASHING METHOD, AND MICROBUBBLE WASHING APPARATUS

BACKGROUND OF THE INVENTION

1. Field of the Invention

The present invention relates to a microbubble washing composition for washing a human body or an animal, a microbubble washing method using the microbubble washing composition, and a microbubble washing apparatus.

2. Description of Related Art

A washing agent containing a surfactant and the like has been used to wash human hair or skin or a pet such as a dog.

However, since a known washing agent cannot reliably remove sebum and old keratin adhering to the surfaces of the pores in a short period of time, dandruff, itching, fallen hair, odor, and the like tend to occur after washing. This makes it difficult to keep the skin clean for a long period of time. Moreover, when washing a person or an animal (pet) suffering from skin disease or having a sensitive skin using a known washing agent or the like, the skin disease gets worse or the skin becomes rough, for example. In recent years, an increased number of people keep a pet such as a dog indoors. Therefore, prevention of skin disease, odor, fallen hair, and the like of the pet has been increasingly demanded.

As related-art technology, JP-A-2-227500 discloses an enzyme-based liquid washing composition containing a nonionic washing compound, a lipase, a lower fatty alcohol, a water-soluble salt of a lower aliphatic carboxylic acid, and a protease in a specific ratio.

JP-A-2-69600 discloses a tablet-type foaming washing agent for washing a nursing bottle which is prepared by adding a specific surfactant to a catabolic enzyme (e.g. protease or lipase) which decomposes milk cake remaining in a nursing bottle, mixing a foaming agent containing sodium hydrogen carbonate and citric anhydride with the mixture, adding an excipient and the like to the mixture, and forming the mixture into a tablet.

JP-A-2006-34473 discloses a tableware washing/drying method which includes a washing step of immersing used tableware in a bath of an aqueous washing medium containing an amylolytic enzyme, a protease, and a lipase and applying vibration to the aqueous washing medium.

JP-T-2004-534528 discloses a preparation containing a specific protease and other enzymes such as protease other than the specific protease, amylase, cellulase, hemicellulase, and/or lipase.

However, the washing agent, the washing method, and the preparation disclosed in the above documents are mainly aimed at washing tableware, clothes, and the like, and are not used for washing a human body or an animal.

SUMMARY OF THE INVENTION

The present invention has been achieved in view of the above-described situation of the related art. An object of the present invention is to provide a microbubble washing composition for washing a human body or an animal, a microbubble washing method using the microbubble washing composition, and a microbubble washing apparatus suitable for carrying out the method which can reliably remove sebum and old keratin adhering to the surfaces of the pores of a human body or an animal in a short period of time and keep the skin clean for a long period of time.

The inventors of the present invention have conducted extensive studies in order to achieve the above object. As a result, the inventors have found that sebum and old keratin adhering to the surfaces of the pores of a human body or an animal and wastes (sebum) inside the pores can be reliably removed in a short period of time so that the skin can be kept clean for a long period of time, skin disease can be prevented, and the healing of skin disease can be accelerated by using a washing liquid obtained by adding a microbubble washing composition including a protease and a lipase to water and introducing microbubbles into the composition when washing human hair or skin or a pet such as a dog. The present invention has been achieved based on the above finding.

A first aspect of the present invention provides a microbubble washing composition according to (1) to (7).

(1) A microbubble washing composition for washing a human body or an animal, the composition comprising a protease and a lipase.

(2) The microbubble washing composition according to (1), wherein the composition contains the protease in an amount of 0.01 to 0.5 wt % based on the total amount of the composition, and contains the lipase in an amount of 0.1 to 1.0 wt % based on the total amount of the composition.

(3) The microbubble washing composition according to (1) or (2), further comprising an alkali metal salt.

(4) The microbubble washing composition according to (3), wherein the alkali metal salt is at least one compound selected from the group consisting of an alkali metal carbonate, an alkali metal hydrogen carbonate, an alkali metal sulfate, an alkali halide, and an alkali metal salt of boron.

(5) The microbubble washing composition according to (3) or (4), wherein the composition contains the alkali metal salt in an amount of 80 to 99.5 wt % based on the total amount of the composition.

(6) The microbubble washing composition according to any one of (1) or (5), further comprising an silica-based desiccant.

(7) The microbubble washing composition according to (6), wherein the composition contains the silica-based desiccant in an amount of 0.01 to 1 wt % based on the total amount of the composition.

According to a second aspect of the present invention, a microbubble washing method according to (8) is provided.

(8) A microbubble washing method for washing a human body or an animal, the method comprising washing a human body or an animal using a washing liquid comprising the microbubble washing composition according any one of (1) to (7) and microbubbles.

According to a third aspect of the present invention, a microbubble washing apparatus according to (9) and (10) is provided.

(9) A microbubble washing apparatus for washing a human body or an animal, the apparatus comprising a discharge section which discharges a washing liquid comprising the microbubble washing composition according any one of (1) to (7), wherein microbubbles are introduced into the washing liquid.

(10) A microbubble washing apparatus for washing a human body or an animal, the apparatus comprising a washing bath in which a washing liquid comprising the microbubble washing composition according any one of (1) to (7) is stored, and a discharge section which discharges water or the washing liquid comprising microbubbles.

According to the present invention, a microbubble washing composition for washing a human body or an animal can be provided which can reliably remove sebum and old keratin adhering to the surfaces of the pores in a short period of time and keep the skin clean for a long period of time when used in combination with microbubbles.

Since the microbubble washing composition according to the present invention does not damage skin, hair, and the like due to low irritating properties, the microbubble washing composition according to the present invention can be safely used for a person having a sensitive skin, an elderly person having a weak skin, or a human or an animal (pet) suffering from skin disease.

The microbubble washing method according to the present invention can reliably remove the cause of an allergy, fallen hair, dandruff, itching, and the like in a short period of time to keep the skin clean for a long period of time, prevent skin disease, and prevent odor for a long period of time by combining the microbubble washing composition according to the present invention and the microbubbles.

Applying the microbubble washing method according to the present invention to a person or an animal suffering from skin disease can keep the skin clean for a long period of time to improve the efficacy of a medicine applied after washing.

Since the microbubble washing method according to the present invention is convenient and safe, the microbubble washing method according to the present invention may be suitably used to wash human hair, a pet, or the body of a person requiring nursing care in the home or in nursing facilities in the same manner as a known washing method.

A significantly excellent washing effect can be obtained by introducing the microbubbles into the microbubble washing composition according to the present invention in comparison with the case of washing using only the microbubbles.

Specifically, the present invention exhibits an effect of reliably removing sebum and old keratin adhering to the surfaces of the pores of a human body or an animal and wastes (sebum) inside the pores in a short period of time and keeping the skin clean for a long period of time, an effect of preventing skin disease, and an effect of accelerating the healing of skin disease.

When washing a pet (animal) such as a dog using the microbubble washing method according to the present invention, the coat of the pet becomes soft.

The microbubble washing apparatus according to the present invention may be suitably used to carry out the microbubble washing method according to the present invention.

DETAILED DESCRIPTION OF THE INVENTION AND PREFERRED EMBODIMENTS

Figure 1:
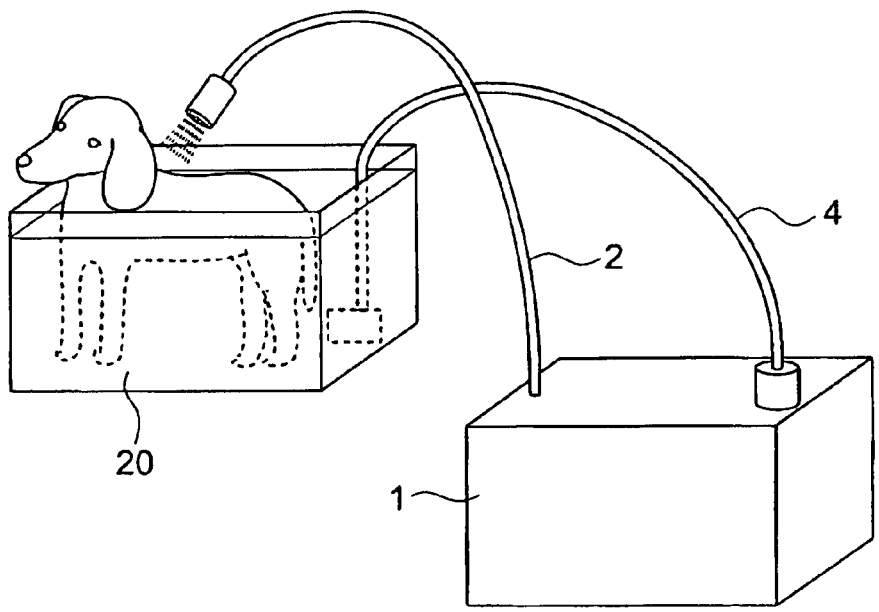
FIG. 1 is a view showing the configuration of an example of a device for carrying out a method of washing a dog according to the present invention.

The present invention is described below in detail in the order of 1) a microbubble washing composition, 2) a microbubble washing method, and 3) a microbubble washing apparatus.

1) Microbubble Washing Composition

A first aspect of the present invention relates to a microbubble washing composition for washing a human body or an animal, the composition comprising a protease and a lipase.

The protease used in the microbubble washing composition according to the present invention (hereinafter may be called "composition according to the present invention") refers to a generic name of enzymes catalyzing hydrolysis of peptide bonds.

The protease has a specific optimum pH, and may be classified as an acidic proteinase, a neutral proteinase, or an alkaline proteinase. In the present invention, any of these proteases may be used without specific limitations.

As non-limiting examples of the protease, chymotrypsin, subtilisin, pepsin, cathepsin D, thermolysin, papain, caspase, bromelain, actinidin, ficin, trypsin, pancreatin, and the like can be given.

These proteases may be used either individually or in combination of two or more.

As specific examples of the protease, Protin AC10F (manufactured by Daiwa Kasei K. K.), Savinase, Alcalase, Esperase, Durazyme (manufactured by Novozymes), Maxapem, Maxatase (manufactured by Gist-brocades), Bioplaze (manufactured by Nagase Biochemicals, Ltd.), and the like can be given.

It is preferable to use at least pancreatin in order to obtain an excellent washing effect. It is more preferable to use pancreatin and other proteases in combination.

The amount of protease used is not particularly limited. The protease is preferably used in an amount of 0.01 to 0.5 wt %, and more preferably 0.2 to 0.3 wt % based on the total amount of the composition.

The lipase used in the composition according to the present invention is an enzyme which hydrolyzes fats into glycerol and a fatty acid.

As non-limiting examples of the lipase, a lipase from *Rhizopus arrhizus*, a lipase from *Aspergillus niger*, and a lipase from a mold such as *Rhizopus delemar*; a lipase from yeast such as *Candida cylindracea*; a lipase from a bacteria such as *Pseudomonas*; a lipase which exists in the digestive tract tissue of a ruminant during a lactation period such as pregastric lipase or oral lipase; pig liver lipase; and the like can be given.

These lipases may be used either individually or in combination of two or more. It is preferable to use two or more types of lipases in order to obtain a more excellent washing effect.

Specific examples of the lipase include Sumizyme NLS (manufactured by Shin-Nihon Kagaku Kogyo, Co., Ltd.), Lipase M "Amano" 10, Lipase M "Amano" 10, Lipase G "Amano" 50, Lipase F-API 5, Lipase AY "Amano" 30G, Lipase R "Amano" G, Lipase T "Amano", Lipase MER "Amano" (manufactured by Amano Enzyme Inc.), Picantase R8000, Picantase A (manufactured by Robin), Toyozyme and LIP (manufactured by Toyobo Co., Ltd.), Lilipase A-10FG, Lilipase AF-5 (manufactured by Nagase ChemteX Corporation), Grindamyl EXEL639 (manufactured by Danisco Culter Japan), Clear-Lens Lipo, Liporaze, Lipex, Lipozyme, Resinase, Paratase, Greasex, Lipopan, Novozyme 435, Lecitase (manufactured by Novozymes), Lipase MY, Lipase OF, Lipase PL, Lipase QLM, Lipase AL, Phospholipase D (manufactured by Meito Sangyo Co., Ltd.), Enzylon AKG (manufactured by Rakuto Kasei Industrial Co., Ltd.), Phospholipase A1 (manufactured by Sankyo Lifetech Co., Ltd.), Lipomod 699L, Lysomax PF (manufactured by Genencor Kyowa Co., Ltd.), and the like.

The lipase used is usually used in an amount of 0.1 to 1.0 wt %, and preferably 0.3 to 0.8 wt % based on the total amount of the composition.

It is preferable that the washing composition according to the present invention further include an alkali metal salt in addition to the protease and the lipase.

The alkali metal salt improves the washing effect, softens water (warm water), and functions as a filler.

The alkali metal salt used is not particularly limited. Examples of the alkali metal salt include alkali metal carbonates such as sodium carbonate and potassium carbonate; alkali metal hydrogen carbonates such as sodium hydrogen carbonate and potassium hydrogen carbonate; alkali metal sulfates such as sodium sulfate and potassium sulfate; alkali halides such as sodium chloride and potassium chloride; alkali metal salts of boron such as sodium tetraborate (borax) and sodium borate; alkali metal silicates such as sodium silicate; alkali metal sulfides such as sodium sulfide; alkali metal nitrates such as sodium nitrate; alkali metal phosphates such as sodium phosphate and sodium dihydrogen phosphate; thiosulfates of an alkali metal such as sodium thiosulfate; and the like.

These alkali metal salts may be used either individually or in combination of two or more.

It is preferable that the composition according to the present invention include at least one alkali metal salt selected from the group consisting of the alkali metal carbonates, the alkali metal hydrogen carbonates, the alkali metal sulfates, the alkali halides, and the alkali metal salts of boron. It is more preferable that the composition include at least one alkali metal salt selected from the group consisting of sodium hydrogen carbonate, sodium sulfate, and borax. It is particularly preferable that the composition include sodium hydrogen carbonate, sodium sulfate, and borax.

The alkali metal salt is usually used in an amount of 80 to 99.5 wt %, and preferably 95 to 99 wt %.

When the washing composition according to the present invention includes sodium hydrogen carbonate, sodium sulfate, and borax, sodium hydrogen carbonate is preferably used in an amount of 10 to 35 wt %, and particularly preferably 20 to 30 wt % based on the total amount of the composition, sodium sulfate is preferably used in an amount of 30 to 70 wt %, and particularly preferably 40 to 60 wt % based on the total amount of the composition, and borax is preferably used in an amount of 10 to 35 wt %, and particularly preferably 20 to 30 wt % based on the total amount of the composition.

It is preferable that the composition according to the present invention further include a silica-based desiccant.

The desiccant stabilizes the potencies of the protease and the lipase. As examples of the silica-based desiccant, Sylysia (porous fine silica powder) and the like can be given.

The silica-based desiccant is usually used in an amount of 0.01 to 1 wt %, and preferably 0.1 to 0.2 wt %.

If necessary, other components may be further added to the composition of the present invention.

As examples of other components, inorganic salts other than the above-mentioned alkali metal salts, a perfume, a coloring agent, an antiseptic agent, an antibacterial agent, a tackiness agent, a therapeutic component, and other additives usually used in a washing agent can be given.

As examples of the inorganic salts other than the alkali metal salts, magnesium salts such as magnesium carbonate and magnesium sulfate; calcium salts such as calcium carbonate, calcium nitrate, calcium thiosulfate, and calcium hydrogen phosphate; alum; and the like can be given.

The amount of inorganic salts used may be appropriately determined insofar as the effects of the microbubble washing composition according to the present invention are not impaired.

Examples of the perfume include essential oils such as abies oil, angelica oil, anisie oil, copaiba balsam, basil oil, bay oil, bergamot oil, birch oil, rosewood oil, cajabute oil, cassia oil, acacia oil, cedar wood oil, chamomile oil, cinnamon oil, cinnamon leaf oil, citronella oil, elemi oil, eucalyptus oil, geranium oil, white-cedar leaf oil, cypress oil, lavandin oil, lavender oil, lemon oil, mint oil, neroli oil, nutmeg oil, oakmoss oil, ocotea oil, patchouli oil, palmarosa oil, plai oil, rose oil, rosemary oil, sandalwood oil, vetiver oil, and ylang ylang oil; synthetic perfumes such as synthetic musk such as limonene, terpinolene, p-cymene, 9-decenol, mugol, myrcenol, borneol, vetiverol, t-butylcyclohexanol, anisole, anethole, safrole, citral, citronellal, cinnamaldehyde, anise aldehyde, cyclamen aldehyde, citral, acetophenone, benzophenone, acetonaphthone, nerone, and nitromusk, geranyl acetate, bornyl acetate, phenylethyl acetate, myrcenyl acetate, methyl benzoate, methyl cinnamate, methyl anthranilate, synthetic oakmoss, and coumarin; and the like.

The perfume is usually used in an amount of 0 to 0.5 wt %, and preferably 0.1 to 0.3 wt %.

As the coloring agent, a dye, a natural pigment, an inorganic dye, and the like may be used.

Examples of the dye include Red No. 2, Red No. 3, Red No. 102, Red No. 104-1, Red No. 105-1, Red No. 106, Red No. 213, Red No. 227, Red No. 230-1, Yellow No. 4, Yellow No. 5, Yellow No. 201, Yellow No. 201-1, Yellow No. 203, Orange No. 205, Green No. 3, Green No. 201, Green No. 204, Blue No. 1, Blue No. 2, Blue No. 205, Violet No. 201, Brown No. 201, and the like.

Examples of the natural pigment include a chlorophyll, a gardenia, a flavonoid, a carotinoide, a quinone, and a riboflavin.

Examples of the inorganic dye include titanium dioxide, talc, kaolin, mica, magnesium silicate, silicic acid anhydride, calcium carbonate, magnesium carbonate, and the like.

These coloring agents may be used either individually or in combination of two or more.

The coloring agent is usually used in an amount of 0 to 0.5 wt %, and preferably 0.1 to 0.2 wt %.

Examples of the antiseptic agent include sodium benzoate, methyl p-hydroxybenzoate, ethyl p-hydroxybenzoate, propyl p-hydroxybenzoate, butyl p-hydroxybenzoate, isobutyl p-hydroxybenzoate, benzyl alcohol, benzalkonium chloride, and the like.

Examples of the tackiness agent include hydroxyethylcellulose, hydroxypropylmethylcellulose, methylcellulose, xanthan gum, polyethylene glycol distearate, polyethylene glycol monostearate, and the like.

The method of producing the composition according to the present invention is not particularly limited. For example, a method may be employed in which a mixture of the protease, the lipase, and other optional components is uniformly mixed and stirred using a stirrer such as a Vert-o-Mix, a Nauta mixer, a universal mixer/stirrer, a ribbon mixer, a V-shaped mixer, or the like to prepare a powder.

The composition according to the present invention can reliably remove sebum and old keratin adhering to the surfaces of the pores of a human body (hair or skin) or an animal in a short period of time and keep the skin clean for a long period of time.

Since the composition according to the present invention does not damage the skin, hair, and the like due to low irritating properties, the composition according to the present invention can be safely used for a person having a sensitive skin, an elderly person having a weak skin, or a human or an animal suffering from skin disease.

2) Microbubble Washing Method

A second aspect of the present invention relates to a microbubble washing method for washing a human body or an animal, the method comprising washing a human body or an animal using a washing liquid comprising the composition according to the present invention and microbubbles.

Specifically, the microbubble washing method according to the present invention includes adding an appropriate amount of the composition according to the present invention to clean water to prepare a washing liquid, introducing microbubbles into the washing liquid, and washing a human body or an animal using the resulting washing liquid.

More specifically, the microbubble washing method according to the present invention includes adding an appropriate amount of the composition according to the present invention to clean water to prepare a washing liquid, introducing microbubbles into the washing liquid, and washing human hair, a human body (skin or foot bottom), or an animal (e.g. dog) using the resulting washing liquid.

When washing human hair, the composition according to the present invention is used to prepare the washing liquid in an amount of usually 1 to 10 g, and preferably 3 to 7 g per 6 to 10 liters of water. When washing human skin or foot bottom, the composition according to the present invention is used to prepare the washing liquid in an amount of usually 1 to 10 g, and preferably 3 to 7 g per 6 to 10 liters of water. When washing an animal such as a dog, the composition according to the present invention is used to prepare the washing liquid in an amount of usually 1 to 10 g, and preferably 3 to 7 g per 6 to 10 liters of water.

The microbubble washing time is usually about one minute to several tens of minutes, although the time varies depending on the type and concentration of the microbubble washing composition, the washing portion, and the like.

The washing temperature is not particularly limited. The washing temperature is preferably 20 to 40° C. from the viewpoint of an excellent washing effect and relaxation.

Since the microbubble washing method according to the present invention can reliably remove sebum and old keratin adhering to the surfaces of the pores in a short period of time and keep the skin clean for a long period of time, skin disease and the like can be prevented, and the cause of an allergy, fallen hair, dandruff, itching, and the like can be removed. Moreover, odor can be suppressed for a long period of time.

The microbubble washing method according to the present invention can keep the skin clean to improve the efficacy of a medicine or the like applied after washing, thereby accelerating the healing of skin disease. Moreover, the microbubble washing method according to the present invention may be suitably used to wash a person who cannot be frequently washed, such as a person requiring nursing care.

The microbubble washing method according to the present invention exhibits a remarkably excellent washing effect in comparison with the case of washing a human body or an animal using water (or warm water) containing only the composition according to the present invention or water (or warm water) containing only microbubbles.

Specifically, the microbubble washing method according to the present invention ensures that the composition according to the present invention and the microbubbles exhibit the effect of reliably removing sebum and old keratin adhering to the surfaces of the pores of a human body or an animal and wastes (sebum) inside the pores in a short period of time and keeping the skin clean for a long period of time, the effect of preventing skin disease, and the effect of accelerating the healing of skin disease. Since the washing liquid containing the microbubbles does not adversely affect the cells of a human body or an animal, does not damage the skin, hair, and the like of a human or an animal, and is environmentally friendly, the washing liquid can be used safely.

The microbubbles are minute bubbles with a diameter of 50 μm or less, and are reduced in size and disappear (completely dissolve) in water, differing from normal bubbles. The microbubbles carry negative ions and disappear in water while bonding to dirt (positive ions) and floating, thereby causing the dirt to float. When using the washing liquid containing the microbubbles to wash a human body or an animal, minute microbubbles can reach the interior of the pores to adsorb and remove wastes.

In order to obtain the washing liquid containing the microbubbles, a microbubble generation device described later is usually used. Since water has a high surface tension, it is impossible to produce bubbles with a diameter of 100 μm or less by normal bubbling.

The microbubble generation device is not particularly limited insofar as the device can produce microbubbles. A known microbubble generation device may be used. Examples of the microbubble generation device include a device which produces microbubbles in a venturi tube (tube with a narrow constriction) or a shower head including an orifice plate (doughnut plate with a center opening) (e.g. JP-A-2006-116518 and Japanese Patent Application No. 2006-77553); a device which produces microbubbles by injecting a liquid mixed with a gas into a main pipe disposed in a liquid and causing the liquid to collide with a collision wall disposed downstream of main pipe (JP-A-2005-334869); a device which produces microbubbles by injecting pressurized air into water through a mesh member or a porous plate with a minute pore size using a pressurized air supply source such as an air pump (JP-A-2006-68631); a device which produces microbubbles by producing a whirling water stream and shearing air using the water stream (JP-A-2003-126665); and the like. When washing human hair, it is preferable to use the microbubble generation device disclosed in Japanese Patent Application No. 2006-77553.

Examples of the method of washing a human body or an animal using the washing liquid containing the microbubbles include (i) a method in which a washing liquid obtained by adding an appropriate amount of the composition according to the present invention to clean water (or warm water) is placed in a container such as a tank, the washing liquid is introduced into the microbubble generation device using an appropriate method, microbubbles are introduced into the washing liquid in the device, and a human body or an animal is washed by discharging the washing liquid containing the microbubbles from a shower nozzle, (ii) a method in which clean water (or warm water) is placed in a washing bath, an appropriate amount of the composition according to the present invention is added to the washing bath to prepare a washing liquid, water (or warm water) containing microbubbles is introduced into the washing liquid from a nozzle connected to the microbubble generation device to prepare a washing liquid containing microbubbles, and a human body or an animal is washed using the resulting washing liquid; and the like. In the present invention, these methods may be used in combination.

When using the method (i), it is preferable to circulate the washing liquid while removing contaminants and the like through a filter in order to efficiently utilize the washing liquid.

3) Washing Apparatus

A third aspect of the present invention relates to a washing apparatus for washing a human body or an animal comprising a discharge section which discharges a washing liquid containing the composition according to the present invention, wherein microbubbles are introduced into the washing liquid, or a washing apparatus for washing a human body or an animal comprising a washing bath in which a washing liquid containing the composition according to the present invention is stored, and a discharge section which discharges water or the washing liquid containing microbubbles.

Examples of the specific configuration of the washing apparatus according to the present invention include (α) a washing apparatus comprising a storage section in which a washing liquid obtained by adding the composition according to the present invention is stored, a microbubble generation section which introduces microbubbles into the washing liquid supplied from the storage section, and a shower nozzle through which the washing liquid containing the microbubbles is discharged, (β) a washing apparatus comprising a washing bath in which a washing liquid obtained by adding the composition according to the present invention is stored, a nozzle section which supplies water (or warm water) containing microbubbles to the washing liquid stored in the washing bath to prepare the washing liquid containing the microbubbles, and a microbubble generation section which supplies the water (or warm water) containing the microbubbles to the nozzle section; and the like.

Examples of the microbubble generation section of the washing apparatus according to the present invention include the microbubble generation devices given as examples of the microbubble generation devices which may be used to obtain the washing liquid containing the microbubbles in the washing method according to the present invention.

Specific examples are described below which wash a human or a pet (animal) using the washing apparatus according to the present invention.

A first specific example is an example of washing a dog (pet).

FIG. 1 is schematically shows a washing apparatus used to carry out this specific example. The washing apparatus shown in FIG. 1 includes a washing bath 20 in which a dog to be washed is placed, and a microbubble generation section 10.

Figure 2:
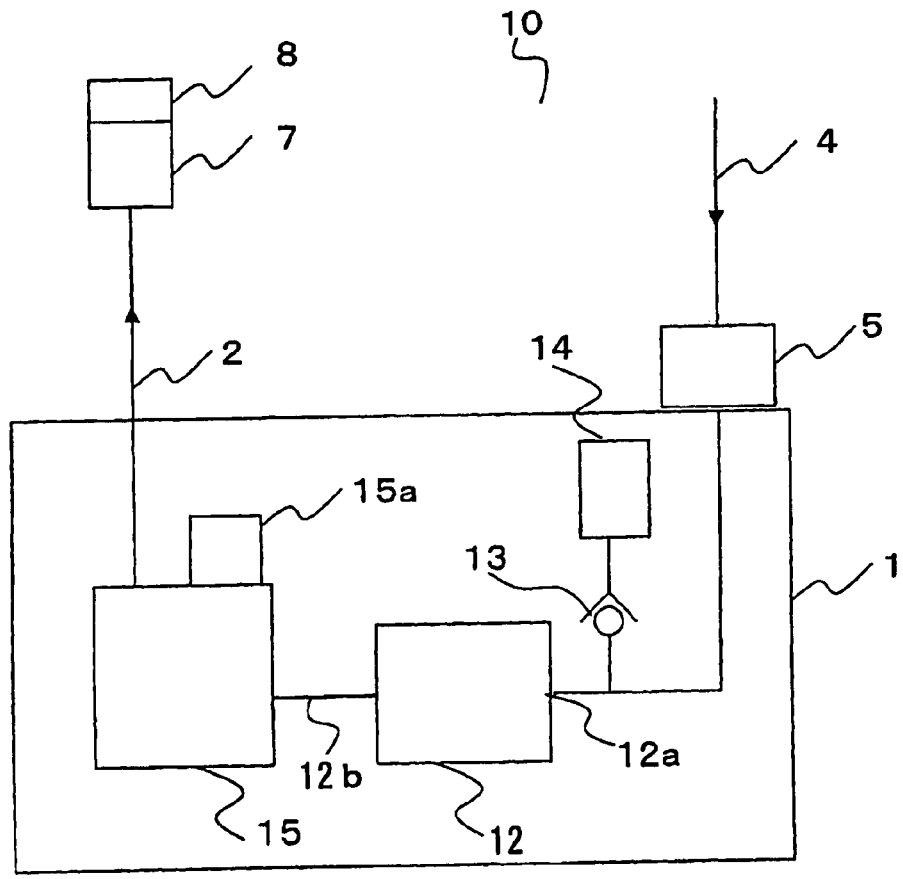
FIG. 2 is a view showing the configuration of a main body 1.

FIG. 2 is an enlarged view of the microbubble generation section 10. The microbubble generation section 10 shown in FIG. 2 includes a main body 1, a suction pipe 4 through which a washing liquid is transported from the washing bath 20 to the main body 1, a filter unit 5 which removes dirt and the like from the washing liquid, a screw pump 12 which pumps the washing liquid and air, an air filter 14 connected to an inlet port 12a of the screw pump 12 through a check valve 13, a gas-liquid separator 15 which mainly discharges unnecessary air to the outside, a discharge pipe 2 through which the washing liquid is transported from the main body 1 to the washing bath 20, a nozzle unit 7 including an orifice plate for producing microbubbles, and a shower head 8 which is disposed on the end of the discharge pipe 2 and through which the washing liquid containing microbubbles is discharged.

A heater unit may be provided in an appropriate place in the main body 1 of the microbubble generation section 10 or the washing bath 20, and the temperature of the washing liquid in the washing bath 20 or the washing liquid discharged from the shower head 8 may be controlled at a predetermined suitable temperature (e.g. about 40° C.) by heating the washing liquid using the heater unit.

First, warm water at about 38° C. is placed in the washing bath 20. The amount of warm water is adjusted so that the body (portion below the head) of the dog is immersed in the warm water in the washing bath, as shown in FIG. 1. The composition according to the present invention is added to the warm water in an amount of 5 to 6 g per 5 to 10 liters of warm water in the washing bath, and the mixture is lightly stirred.

The washing composition used in this example is prepared by mixing borax: 25 wt %, sodium hydrogen carbonate: 25 wt %, sodium sulfate: 50 wt %, pancreatin: 0.1 wt %, Protin AC: 0.15 wt %, lipase: 0.5 wt %, Sylysia: 0.15 wt %, perfume: 0.2 wt %, and dye: 0.12 wt % using a stirrer.

The end of the suction pipe 4 is placed at the bottom of the washing bath 20. The washing liquid in the washing bath 20 is introduced into the screw pump 12 from the suction pipe 4 through the filter unit 5 by operating the screw pump 12. An appropriate amount of air is pumped into the screw pump 12 through the air filter 14.

In the screw pump 12 into which the washing liquid and the air are introduced, bubbles are shorn and reduced in size by an impeller which is rotated in the screw pump 12, whereby air is dissolved in the washing liquid. The washing liquid in which air is dissolved is discharged from the outlet port 12b of the screw pump 12 together with undissolved bubbles and supplied to the gas-liquid separator 15. In the gas-liquid separator 15, dissolution of air in the washing liquid is promoted, and undissolved air is discharged to the atmosphere through a relief valve 15a provided at the upper portion of the gas-liquid separator 15.

The washing liquid in which a large amount of air is dissolved passes through the discharge pipe 2 from the gas-liquid separator 15, is discharged from the shower head 8 provided on the end of the discharge pipe 2 placed at the bottom of the side surface of the washing bath 20, and is returned to the washing bath 20.

The nozzle unit 7 is attached to the shower head 8. A number of orifice plates are provided in the nozzle unit 7 in series. The washing liquid is compressed and expanded each time the washing liquid passes through the orifice plate, and air dissolved in the washing liquid produce microbubbles in the washing liquid. The washing liquid containing the microbubbles is discharged into the washing bath from the shower head 8.

The washing bath, into which the washing liquid containing the microbubbles discharged, is filled with minute bubbles and becomes clouded. Since the microbubbles have a small buoyancy, the microbubbles float in the water for a long period of time without immediately reaching the water surface, whereby the effects are maintained.

After the washing liquid in the washing bath 20 is filled with the microbubbles, the operation of the screw pump 12 may be stopped, or the screw pump 12 may be continuously operated. The dog is bathed in the washing bath 20 for about 5 to 15 minutes to wash the body of the dog.

The head of the dog which is not immersed in the washing liquid in the washing bath 20 may be washed by lifting the shower head 8 on the end of the discharge pipe 2 placed at the bottom of the side surface of the washing bath 20 and discharging the washing liquid containing the microbubbles from the shower head 8 onto the dog's head, for example.

When the washing liquid containing the microbubbles contacts the body of the dog, the protease and the lipase in the washing composition according to the present invention placed in the washing bath effectively decompose and remove the sebum and old keratin adhering to the surfaces of the pores of the dog, whereby the surface of the body of the dog is washed. Since the microbubbles can easily enter the interior of the pores after the dirt adhering to the surfaces of the pores is decomposed and removed, wastes (sebum) and the like inside the pores can be adsorbed due to the surface tension and effectively removed.

The microbubbles contained in the washing liquid break on the surface of the body of the dog to produce pulse impact, and the dirt and the like adhering to the body of the dog can be effectively removed by the microvibration.

As described above, since a person doing the washing need not scrub the dog's skin using a sponge or the like, wastes inside the pores can be reliably removed in a short period of time without damaging the dog's skin and hair.

After the completion of washing, the washing composition is rinsed away by spraying water (or warm water) on the body of the dog from a normal shower nozzle or the like.

When washing the dog using the washing apparatus according to the present invention, positive effects, such as (a) the coat becomes soft, (b) the skin becomes pink, (c) animal odor is reduced, (d) skin troubles such as an allergy, dandruff, and itching are reduced, (e) fallen hair is reduced, and (f) the skin can be kept clean for a long period of time can be obtained, in comparison with the case of washing the dog using a known pet washing agent.

In particular, the period of time until odor occurs after washing is nearly doubled. Moreover, since the skin can be kept clean for a long period of time after washing, the present invention is effective for preventing and healing skin disease. Since the present invention uses the washing liquid including the composition according to the present invention and the microbubbles, skin irritation occurs to only a small extent. Moreover, the washing time is reduced, and the washing agent is easily rinsed away. Therefore, the burden on the dog (animal) is reduced.

An example of a method of washing human hair is described below as a second specific example.

This method uses an apparatus similar to the washing apparatus used in the method of washing the dog except that the washing bath 20 is omitted, the discharge pipe 2 and the suction pipe 4 are connected to a washing cap which can be fitted onto the human head in the same manner as a cap, and a cartridge tank (storage section) is provided in the main body 1.

The washing cap is fitted onto the human head so that the entire hair is positioned in the space formed when fitting the washing cap, and has a structure in which the washing liquid discharged into the washing cap does not leak to the outside.

The cartridge tank is filled with a washing liquid similar to that prepared in the washing bath 20.

According to such a washing apparatus, the washing liquid is discharged from the main body 1 into the washing cap through the discharge pipe 2, whereby the head can be washed. The discharged washing liquid is transferred from the washing cap into the filter unit 5 through the suction pipe 4. After removing any loose hair, dandruff and the like through the filter unit 5, the washing liquid is collected in the cartridge tank.

The washing liquid collected in the cartridge tank is pumped into the screw pump 12 in the same manner as for the washing apparatus used in the method of washing the dog. In the screw pump 12, air is dissolved in the washing liquid, and the washing liquid is transferred from the gas-liquid separator 15 to the washing cap through the discharge pipe 2.

The nozzle unit 7 similar to that used in the washing apparatus used in the method of washing the dog is provided in the connection portion between the discharge pipe 2 and the washing cap.

The washing liquid is provided with a large number of microbubbles when passing through the nozzle unit 7, dispersed in a number of directions, and discharged into the washing cap.

When washing hair using the washing apparatus according to the present invention, the hair and the scalp are not damaged since it is unnecessary to directly scrub the hair and the scalp. Moreover, wastes inside the pores can be reliably removed in a short period of time.

After the completion of washing, the washing cap is removed from the head, and the washing agent is removed by rinsing the head with water from a shower nozzle or the like.

The washing apparatus according to the present invention can suppress dandruff, itching, and fallen hair without damaging the scalp and hair, and can safely wash the hair of a person suffering from a scalp disease or a person having a sensitive skin (e.g. the scalp gets rough or an allergy occurs when using a known washing agent).

The present invention is not limited to the above embodiments. Various modifications may be made without departing from the scope of the present invention.

The washing apparatus according to the present invention can safely and easily wash a human body (particularly hair, skin, and foot bottom) or a pet, and keep the skin clean for a long period of time.

Since the washing apparatus according to the present invention is convenient and safe and exhibits an excellent washing effect, the washing apparatus according to the present invention may be utilized to wash a human or a pet in the home; to wash the human body, hair, foot bottom, and the like in a public bath, a hospital, a nursing home, a nursing-care facility, and the like; to wash the human hair, foot bottom, and the like in a barbershop, a beauty salon and the like; to wash a pet in an animal hospital, an animal hotel, and the like; and the like.

What is claimed is:

1. A microbubble washing composition for washing a human body or an animal consisting of at least one protease, at least one lipase and at least one alkali metal salt selected from the group consisting of alkali metal carbonates, alkali metal hydrogen carbonates, alkali metal sulfates, alkali halides, and alkali metal salts of boron.

2. A microbubble washing method for washing a human body or an animal, the method comprising washing a human body or an animal using microbubbles and a washing liquid composition consisting of at least one protease, at least one lipase and at least one alkali metal salt selected from the group consisting of alkali metal carbonates, alkali metal hydrogen carbonates, alkali metal sulfates, alkali halides, and alkali metal salts of boron.

3. The method according to claim 2, wherein the at least one alkali metal salt in the composition is present in an amount of 80 to 99.5 wt % based on the total amount of the composition.

4. The method of washing, wherein the washing liquid composition consists of the at least one protease, the at least one lipase, the at least one alkali metal salt, and at least one silica-based desiccant.

5. The method according to claim 4, wherein the composition contains the at least one silica-based desiccant in an amount of 0.01 to 1 wt % based on the total amount of the composition.

6. The microbubble washing composition according to claim 1, wherein the alkali sulfates are sodium sulfate or potassium sulfate.

7. The method according to claim 2, wherein the at least one protease in the composition is present in an amount of 0.01 to 0.5 wt % based on the total amount of the composition, and the at least one lipase is present in an amount of 0.1 to 1.0 wt % based on the total amount of the composition.

8. The method according to claim 2, wherein the microbubbles have a diameter of 50 μm or less.

9. The method according to claim 2, wherein the microbubbles are negatively charged.

10. The method according to claim 9, which further comprises filtering out contaminants released from the subject during the washing step.

11. The microbubble washing method according to claim 2, wherein the alkali sulfates are sodium sulfate or potassium sulfate.

* * * * *